United States Patent [19]

Kumakura et al.

[11] 4,177,107

[45] Dec. 4, 1979

[54] PROCESS FOR PRODUCING COMPOSITION CONTAINING INSOLUBILIZED ENZYME AND/OR INSOLUBILIZED BACTERIAL CELLS

[75] Inventors: Minoru Kumakura; Masaru Yoshida; Isao Kaetsu, all of Takasaki, Japan

[73] Assignee: Japan Atomic Energy Research Institute, Tokyo, Japan

[21] Appl. No.: 763,601

[22] Filed: Jan. 28, 1977

[30] Foreign Application Priority Data

Jan. 31, 1976 [JP] Japan ................................. 51-9702

[51] Int. Cl.$^2$ ................................................ C07G 7/02
[52] U.S. Cl. ..................................... 435/176; 435/181
[58] Field of Search ................... 195/63, 68, DIG. 11, 195/59

[56] References Cited

U.S. PATENT DOCUMENTS

| 3,577,512 | 5/1971 | Shepherd | 424/21 |
|---|---|---|---|
| 3,859,169 | 1/1975 | O'Driscoll | 195/63 |
| 3,860,490 | 1/1975 | Guttag | 195/108 |
| 3,871,964 | 3/1975 | Huper | 195/63 |
| 3,933,587 | 1/1976 | Maeda | 195/68 |
| 3,962,038 | 6/1976 | Kawashima | 195/68 |
| 4,025,391 | 5/1977 | Kawashima et al. | 195/68 |

FOREIGN PATENT DOCUMENTS

| 48-92466 | 4/1973 | Japan. |
| 50-78640 | 2/1975 | Japan. |
| 51-26286 | 2/1976 | Japan. |

*Primary Examiner*—Lionel M. Shapiro
*Attorney, Agent, or Firm*—Browdy and Neimark

[57] ABSTRACT

A process for producing a composition containing insolubilized enzyme and/or insolubilized bacterial cells which comprises (i) the step of mixing (a) an aqueous solution of enzyme and/or an aqueous dispersion of bacterial cells, (b) at least one porous adsorbent and (c) at least one vitrifiable monomer.

4 Claims, No Drawings

PROCESS FOR PRODUCING COMPOSITION CONTAINING INSOLUBILIZED ENZYME AND/OR INSOLUBILIZED BACTERIAL CELLS

BACKGROUND OF THE INVENTION

This invention relates to a process for producing a composition containing insolubilized enzyme and/or insolubilized bacterial cells which can be continuously employed for a long period or which can be repeatedly employed many times in a batch system.

Recently the enzyme industry has become important and has made remarkable progress in producing medicine and food by utilizing enzyme or cells to carry out a variety of reactions.

In the prior art the enzyme reaction was effected by using enzyme solution. In this case, however, after the reaction is completed, the enzyme solution employed in the reaction cannot be reused, because the used enzyme solution contains the resulting reaction product. Therefore, since the enzyme solution employed in the one reaction must be removed from the reaction system, the batch system must be used for the enzyme reaction. In other words, in an enzyme reaction using enzyme solution, the maximum effectiveness of the enzyme is not obtained.

U.S. Pat. No. 3,860,490 by Guttag discloses that microorganisms are entrapped in a hydrophilic acrylate. However, the Guttag invention relates to the quick or controlled release of living microorganisms such as bacteria, molds, yeast and viruses or to providing limited contact between the microorganism and an environment on which it acts. The object of the Guttag invention is to store living microorganisms so that they can be released or can act in an appropriate area and/or at an appropriate time. That is, the object of Guttag invention is to keep the microorganisms dry or out of contact with air until use.

U.S. Pat. No. 3,859,169 by O'Driscoll et al discloses that enzymes are provided in gels.

U.S. Pat. No. 3,871,964 by Huper et al discloses that polypeptide such as enzymes are rendered water-soluble by bonding to a cross-linked copolymer.

U.S. Ser. No. 606,209 filed on Aug. 20, 1975 by Kaetsu et al discloses a process for producing polymer-enzyme composition containing insolubilized enzyme and/or bacterial cells, characterized by irradiating the mixture of a vitrifiable monomer and enzyme and/or cells by means of ionizing radiation at a temperature of less than 0° C. U.S. Ser. No. 688,081 filed on May 19, 1976 by Kaetsu et al discloses a similar process. The ratio of the activity of the enzyme-polymer composition of U.S. Ser. Nos. 606,209 and 688,081 to the activity of an aqueous solution containing the same enzyme (sometimes referred to as the degree of activity maintained) is as low as 60% or less. In addition, when the enzyme-polymer composition prepared according to U.S. Ser. Nos. 606,209 and 688,081 can be used for a long period under severe conditions, the enzyme is likely to be released. Therefore, the enzyme reaction can not continuously be carried out for a long period in a column by using said enzyme-polymer composition.

U.S. Pat. No. 3,962,038 by Kawashima et al discloses that enzymes are entrapped in polymers of acrylamide, bisacrylamide, acrylic acid, sodium acrylate, potassium acrylate and calcium acrylate. The monomers employed in Kawashima et al are in a crystalline state at a temperature less than 0° C. Polymerizability of the crystallizable monomer is lowered at a temperature less than 0° C., because molecular motion of the monomer is restricted by formation of the crystal latice.

However, the prior processes for entrapping enzyme or bacterial cells had the disadvantages that the enzyme is likely to release from the polymer. Therefore, compositions containing insolubilized enzyme prepared according to the prior processes can be used only for a short period in a continuous process, and can not repeatedly be used many times in a batch process.

SUMMARY OF THE INVENTION

The inventors of the present invention found that when enzyme is mixed with a vitrifiable monomer as well as a porous adsorbent, the composition obtained by irradiating the resulting mixture by means of an ionizing radiation has a high degree of activity maintained. This invention is based on this discovery.

Therefore, one object of this invention is to provide a composition containing insolubilized enzyme and/or insolubilized bacterial cells, in which the enzyme and/or cells are firmly entrapped in the composition.

This invention relates to a process for producing a composition containing insolubilized enzyme and/or insolubilized bacterial cells which comprises (i) the step of mixing (a) an aqueous solution of enzyme and/or an aqueous dispersion of bacterial cells, (b) at least one porous absorbent and (c) at least one vitrifiable monomer selected from the group consisting of a compound having the formula:

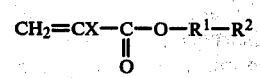

wherein X is H or methyl, $R^1$ or $+CH_2+_n$ wherein n is an integer of 1 to 6,

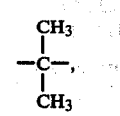

$+CH_2-CH_2-O+_m$ wherein m is an integer of 2 or more, preferably 2 to 6, or

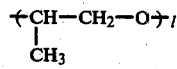

wherein l is an integer of 2 or more, preferably 2 to 6, and when $R^1$ is $+CH_2+_n$ or

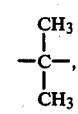

$R^2$ is —OH, —OCH$_3$ or

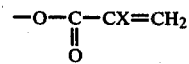

wherein X is as defined above, when $R^1$ is $+CH_2-CH_2-O+_m$ or

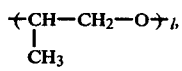

$R^2$ is hydrogen, methyl, or

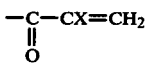

wherein X is as defined above; or a compound having the formula:

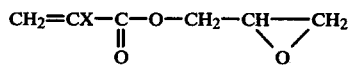

wherein X is as defined above; a compound having the formula

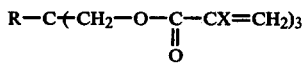

wherein R is ethyl, n-propyl or isopropyl and X is as defined above; and mixtures thereof, and (ii) the step of irradiating the mixture by means of an ionizing radiation at a temperature of less than −10° C., preferably from 80° C. to −25° C.

Even when the composition prepared according to the present invention is continuously used for enzyme reaction, the enzyme is not released from the composition. It is critical that the enzyme or the cells be mixed with a porous adsorbent as well as at least one vitrifiable monomer. When one of the porous adsorbent and the vitrifiable monomer is absent, the enzyme or cells can not firmly be entrapped only in one of the adsorbent and polymer obtained from the monomer.

DETAILED DESCRIPTION OF THE INVENTION

Examples of the porous adsorbents include molecular sieves, activated carbon, Kanuma soil, porous argil, porous ion-exchange resin, particulate calcium sulfate and mixtures thereof. Molecular sieves and Kanuma soil are preferred. Kanuma soil is most preferred.

The "Kanuma soil" is the soils that are found in Kanuma district of Japan. This is sold under the trade name of "Kanuma soil" from various companies. The Kanuma soil is generally used for gardening.

Examples of the vitrifiable monomers include hydroxyethyl methacrylate, hydroxyethyl acrylate, hydroxypropyl methacrylate, hydroxypropyl acrylate, glycidylacrylate, glycidylmethacrylate, diethyleneglycol methacrylate, diethyleneglycol acrylate, triethyleneglycol methacrylate, triethyleneglycol acrylate, tetraethyleneglycol methacrylate, tetraethyleneglycol acrylate, polyethyleneglycol methacrylate, polyethyleneglycol acrylate, diethyleneglycol dimethacrylate, diethyleneglycol diacrylate, triethyleneglycol dimethacrylate, triethyleneglycol diacrylate, tetraethyleneglycol dimethacrylate, tetraethyleneglycol diacrylate, polyethyleneglycol dimethacrylate, polyethyleneglycol diacrylate, methoxydiethylene glycol dimethacrylate, methoxydiethyleneglycol diacrylate, methoxytriethyleneglycol dimethacrylate, methoxytriethyleneglycol diacrylate, methoxytetraethyleneglycol dimethacrylate, methoxytetraethyleneglycol diacrylate, methoxypolyethyleneglycol dimethacrylate, methoxypolyethyleneglycol diacrylate, neopentylglycol dimethacrylate, neopentylglycol diacrylate, trimethylol propane trimethacrylate, trimethylolpropane triacrylate, trimethylolbutane triacrylate, trimethylolbutane trimethacrylate, butanediol monomethacrylate, butanediol monoacrylate, pentanediol monomethacrylate, pentanediol monoacrylate, hexanediol monomethacrylate, hexanediol monoacrylate, heptanediol monomethacrylate, heptanediol monoacrylate, butanediol dimethacrylate, butanediol diacrylate, pentanediol dimethacrylate, pentanediol diacrylate, hexanediol dimethacrylate, hexanediol diacrylate, heptanediol dimethacrylate, heptanediol diacrylate, ethyleneglycol dimethacrylate, ethyleneglycol diacrylate, propyleneglycol dimethacrylate, propyleneglycol diacrylate, dipropyleneglycol dimethacrylate, dipropyleneglycol diacrylate, dipropyleneglycol dimethacrylate, dipropyleneglycol diacrylate, tripropyleneglycol dimethacrylate and tripropyleneglycol diacrylate. Hydroxyethyl acrylate, hydroxypropyl methacrylate, glycidylacrylate, glycidylmethacrylate, tetraethyleneglycol methacrylate, tetraethyleneglycol acrylate, diethyleneglycol dimethacrylate, diethyleneglycol acrylate, polyethyleneglycol dimethacrylate, polyethyleneglycol diacrylate, neopentylglycol dimethacrylate, neopentylglycol diacrylate, trimethylol propane trimethacrylate, trimethylolpropane triacrylate, butanediol dimethacrylate, butanediol diacrylate, hexanediol dimethacrylate, hexanediol diacrylate, ethyleneglycol dimethacrylate, and ethyleneglycol diacrylate are preferred. One monomer mixture thereof may be used as vitrifiable monomer.

According to the present invention, a variety of enzymes and/or a variety of the bacterial cells can be insolubilized without losing the activity of the enzyme and cells.

The enzymes to be immobilized or to be made insoluble by the present invention include urease, alcohol dehydrogenase, lactic dehydrogenase, malic dehydrogenase, glycose oxidase, diamine oxidase, glycose oxidase-catalase, D-amino acid oxidase, liposidase, uricase, ribonuclease, hexokinase, lipase, alkaline phosphatase, acidic phosphatase, nucleoedase, deoxyribonuclease, α-amylase, β-amylase, glucoamylase, glycoseisomerase, cellulase, hemicellulase, β-glucosidase, invertase, anthoxyanase, narindinase, hesperidinase, β-glucuronidase, hyaluronidase, alkaline protease, semialkaline protease, acidic protease, thermorairin, collagenase, pepsin-pepsinagen, aminopeptidase, rennin, trypsin-trypsinogen, chymotrypsinogen, elastase, enterodinase, acrylase, arginase, L-glutamic acid decarboxylase, L-lysine decarboxylase, and papain.

The bacterial cells to be immobilized or to be made insoluble by the present invention include cells containing the above mentioned enzymes, *Aerobacter aerogenes, Azotobacter vinelandi, Bacillus subtilis, Escherrichia coli* and *micrococcus lysodeikticus*. Other enzymes and bacterial cells can be immobilized or made insoluble according to the present invention.

In the present invention, diatomaceous earth, kaolin, cellulose, its derivatives, protein materials, such as gelatin, agar, collagen, silica gel, alumina, silicate, talc, clay, or synthetic resins may be incorporated in the composition in order to increase the adsorbing rate of the enzyme or cells.

The blending operation of the enzyme and/or the bacterial cells with the porous adsorbent and the vitrifiable monomer can be carried out by any known method, such as mechanical method. The uniformly dispersed mixture of each component is pasty or in a thick slurry state. When the components are thoroughly mixed, a pasty material or a thick slurry is formed, in which each component is uniformly dispersed. The mixture of the enzyme and/or cells, the porous adsorbent and the vitrifiable monomer is irradiated with an ionizing radiation to polymerize the monomer, whereby the enzyme and/or cells is insolubilized. The ionizing radiation includes, for example, alpha-rays, beta-rays, electron beam, gamma-rays, X-rays and mixed rays emitted from nuclear reactor. The total dose of irradiation may be in the range of from $10^2$R to $10^7$R, preferably from $10^3$ to $10^6$R; and the dose rate of irradiation may be in the range of from $10^2$R/hr to $10^9$R/hr, preferably from $10^3$ to $10^8$R/hr. The irradiation or polymerization is carried out at a temperature of less than $-10°$ C., preferably from $-80°$ C. to $-25°$ C. The irradiation can be carried out even at a temperature of less than $-200°$ C.

The proportion of each component in the mixture to be irradiated is not critical. However, the ratio of the adsorbent to the vitrifiable monomer may be in the range of from 8:2 to 2:8 by weight, preferably from 6:4 to 4:6. Conveniently, less than 50 parts by weight of enzyme and/or bacterial cells are used per 100 parts of the combined weight of the monomer and the adsorbent. Preferably, the enzyme and/or the cells in the range of from 5 parts to 30 parts by weight is used. The ratio of water to the monomer may be in the range of from 99:1 to 20:80.

The enzyme and cells-containing composition which keeps high activity of the enzyme and/or cells, and in which the enzyme and/or cells are firmly entrapped in the composition can be obtained according to the present invention. The reason is thought as follows:

The adsorbent adsorbs the enzyme and/or cells onto its surface or into its void, and the enzyme and/or cells-adsorbing adsorbent is firmly entrapped in the polymer obtained by polymerizing the monomer. As a result, network structure is formed altogether. Since the size of enzyme and of cells is small, the enzyme and cells are more difficultly entrapped in the composition than the enzyme and/or cells-adsorbing adsorbent is entrapped. Therefore, the enzyme or cells are likely to be released from enzyme (cells)-polymer composition not containing any adsorbent. On the other hand, since the enzyme (cells)-polymer composition containing the porous adsorbent is in a network structure, the reactant for enzyme reaction can be penetrated in the porous composition, and is likely to contact the enzyme or bacterial cells. Therefore, the composition prepared according to the present invention has high activity of the enzyme or bacterial cells.

One enzyme or one kind of bacterial cells may be insolubilized according to the present invention, two or more enzymes or two or more kinds of cells may also be insolubilized. Furthermore, a mixture of enzyme and cells may be insolubilized.

By "enzyme reaction" we means a reaction in which an enzyme or cells are employed as a catalyst, an initiator or a reactant.

By the insolubilization of enzyme or cells we means that the enzyme or cells are held by the polymer so that enzyme or cells may be employed in the enzyme reaction many times or continuously.

The reason why the polymerization is carried out at a low temperature is as follows: The enzyme and the bacterial cells are instable or are likely to be deactivated, so it is necessary that the polymerization of monomer be carried out at a low temperature for insolubilizing the enzyme or cells. Therefore, the use of ionizing radiation as polymerization means is critical for allowing the polymerization to occur at a low temperature.

A crystallizable monomer is in a crystalline state at a temperature less than $0°$ C.

Polymerizability of a crystallizable monomer is lowered at a temperature less than $0°$ C., because molecular motion of the monomer is restricted by formation of the crystal lattice at this temperature. In addition, the crystallizable monomer is not a homogeneous dispersion medium, that is the mixture of the crystallizable monomer and the enzyme, etc. does not become a homogeneous dispersion in which he enzyme, etc. is uniformly dispersed. Therefore, when the mixture of the crystallizable monomer and the enzyme, etc. is polymerized at a temperature less than $0°$ C., the enzyme, etc. is not firmly entrapped in the resulting polymer.

On the other hand, the vitrifiable monomer of the present invention is not in a crystalline state at a temperature less than $0°$ C., but is in the supercooled state at the temperature. Polymerizability of the vitrificable monomer is very great at a temperature less than $0°$ C., because the molecular motion of the monomer is not restricted.

In addition, when the vitrifiable monomer employed in the present invention is cooled to a temperature less than $0°$ C., the monomer becomes a highly viscous liquid in a supercooled state. The enzyme, etc. is uniformly dispersed in the monomer in a highly viscous liquid. Therefore, when the mixture of the highly viscous monomer and the enzyme is polymerized at a low temperature, the enzyme, etc. can be firmly entrapped in the resulting polymer.

The present invention is further illustrated, but in no way limited, by the following Examples. The percent and part are based on weight unless otherwise specified.

EXAMPLE 1

Thirty parts of glucose isomerase, 40 parts of Kanuma soil, 100 parts of a buffer solution and 45 parts of hydroxyethyl methacrylate were thoroughly mixed to obtain a uniform dispersion. The resulting dispersion was irradiated with gamma-rays from cobalt 60 having a dose rate of $5 \times 10^5$ R/hr at a total dose of $10^6$R at a temperature of $-78°$ C. to polymerize the monomer. The resulting composition was powderized. The powderized composition was added to a 50% solution of glucose in a solution containing 0.01 M of $MgSO_4.7H_2O$. The glucose was converted to fructose at pH of 7 batchwise. Four ml of sample was withdrawn from the resulting, and the sample was rendered colored through cystein-carbasole reaction. The amount of fructose thus formed was determined from color comparison of 560 m$\mu$, whereby the activity of the composition prepared according to this Example was calculated.

Control test was effected by following the above experiment except that the enzyme was used in the state of solution. Similarly, the activity of the enzyme solution was obtained. The ratio of the activity of the enzyme-polymer composition of the present invention obtained in Example 1 to the activity of the enzyme solution was 90%. Even when the enzyme reaction was repeatedly carried out many times by using the same composition, the activity of the composition was not lowered.

EXAMPLE 2

Thirty parts of glucose isomerase, 40 parts of Kanuma soil, 110 parts of a buffer solution and 40 parts of hydroxymethyl methacrylate were thoroughly mixed to obtain a uniform dispersion. The resulting dispersion was irradiated with gamma-rays from cobalt 60 having a dose rate of $1 \times 10^6$ R for an hour at a temperature of $-78°$ C. to polymerize the monomer. The resulting composition was powderized. The powderized composition was packed in a column having a diameter of 1.5 cm and a length of 2.0 cm. A 50% solution of glucose in a solution containing 0.01 M of $MgSO_4 \cdot 7H_2O$ was passed through the column at a space velocity of 1 at 65° C. for one month to convert glucose to fluctose. The conversion was 40% at the start of the reaction; whereas the conversion was 30% at the end point of the reaction.

Comparative Example 1

The procedure of Example 1 was repeated except that Kanuma soil is not used. The ratio of the activity of the enzyme-polymer not containing any adsorbent obtained in Comparative Example 1 to the activity of the enzyme solution was 58.5%.

What we claim is:

1. A process for producing a composition containing insolubilized enzyme and/or insolubilized bacterial cells which comprises (i) the step of mixing (a) an aqueous solution of enzyme and/or an aqueous dispersion of bacterial cells, (b) at least one porous adsorbent and (c) at least one vitrifiable monomer selected from the group consisting of a compound having the formula:

$$CH_2=CX-\underset{\underset{O}{\|}}{C}-O-R^1-R^2$$

wherein X is H or methyl, $R^1$ is $+CH_2+_n$ wherein n is an integer of 1 to 6,

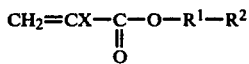

$+CH_2-CH_2-O+_m$ wherein m is an integer of 2 or more, or

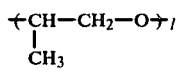

wherein l is an integer of 2 or more, and when $R^1$ is $+CH_2+_n$ or

$R^2$ is —OH, —OCH$_3$ or

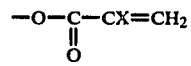

wherein X is as defined above, when $R^1$ is $+CH_2-CH_2-O+_m$ or

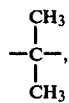

$R^2$ is hydrogen, methyl, or

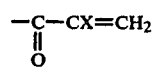

wherein X is as defined above; or a compound having the formula:

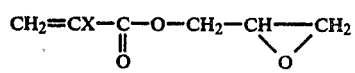

wherein X is as defined above; a compound having the formula

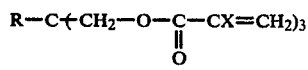

wherein R is ethyl, n-propyl or isopropyl and X is as defined above; and mixtures thereof, and (ii) the step of irradiating the mixtures by means of an ionizing radiation at a temperature of less than $-10°$ C.

2. The process as defined in claim 1, wherein the irradiation is carried out at a temperature in the range of from $-80°$ C. to $-25°$ C.

3. The process as defined in claim 1, wherein the monomer is selected from the group consisting of hydroxyethyl acrylate, hydroxypropyl methacrylate, glycidylacrylate, glycidylmethacrylate, tetraethyleneglycol methacrylate, tetraethyleneglycol acrylate, diethyleneglycol dimethacrylate, diethyleneglycol acrylate, polyethyleneglycol dimethacrylate, polyethyleneglycol diacrylate, neopentylglycol dimethacrylate, neopentylglycol diacrylate, trimethylol propane trimethacrylate, trimethylolpropane triacrylate, butanediol dimethacrylate, butanediol diacrylate, hexanediol dimethacrylate, hexanediol diacrylate, ethyleneglycol dimethacrylate, ethyleneglycol diacrylate and mixtures thereof.

4. The process as defined in claim 1, wherein the adsorbent is selected from the group consisting of molecular sieves, activated carbon, Kanuma soil, porous argil, porous ion-exchange resin, particulate calcium sulfate and mixtures thereof.

* * * * *